US009216126B2

(12) United States Patent
Schuele et al.

(10) Patent No.: US 9,216,126 B2
(45) Date of Patent: Dec. 22, 2015

(54) TABLE ADAPTER WITH JOINT ASSEMBLY

(71) Applicant: pro med instruments GmbH, Freiburg i.Br (DE)

(72) Inventors: Matthias E. Schuele, Freiburg (DE); Tilman Niederfuehr, Freiburg (DE)

(73) Assignee: PRO MED INSTRUMENTS GMBH, Freiburg (DE)

( * ) Notice: Subject to any disclaimer, the term of this patent is extended or adjusted under 35 U.S.C. 154(b) by 0 days.

(21) Appl. No.: 14/012,868

(22) Filed: Aug. 28, 2013

(65) Prior Publication Data

US 2014/0059771 A1    Mar. 6, 2014

Related U.S. Application Data

(60) Provisional application No. 61/694,246, filed on Aug. 28, 2012.

(51) Int. Cl.
| | |
|---|---|
| A61G 13/12 | (2006.01) |
| A61B 6/04 | (2006.01) |
| A61B 19/00 | (2006.01) |
| A47C 7/38 | (2006.01) |
| A61B 5/055 | (2006.01) |

(52) U.S. Cl.
CPC ............ *A61G 13/121* (2013.01); *A61B 6/0421* (2013.01); *A61B 19/203* (2013.01); *A47C 7/383* (2013.01); *A61B 5/0555* (2013.01)

(58) Field of Classification Search
CPC .. A61B 5/0555; A61B 19/203; A61B 6/0421; A47C 7/383; A61G 13/121
USPC ................................ 5/622, 601, 621; 606/59
See application file for complete search history.

(56) References Cited

U.S. PATENT DOCUMENTS

| | | | |
|---|---|---|---|
| 1,839,726 A | 1/1932 | Arnold |
| 2,586,488 A | 2/1952 | Smith |
| 2,594,086 A | 4/1952 | Smith |
| 3,522,799 A | 8/1970 | Gauthier |

(Continued)

FOREIGN PATENT DOCUMENTS

| | | |
|---|---|---|
| DE | 9116 002 | 2/1992 |
| WO | WO 97/40764 | 4/1997 |

(Continued)

OTHER PUBLICATIONS

Partial European Search Report dated Feb. 6, 2006 for Application No. EP 05292169.

(Continued)

*Primary Examiner* — Peter M Cuomo
*Assistant Examiner* — Brittany Wilson
(74) *Attorney, Agent, or Firm* — Frost Brown Todd LLC

(57) ABSTRACT

A table adapter and joint assembly are configured for use with a table during a medical procedure, e.g. a medical imaging procedure or combined imaging and surgical procedure. The table adapter is connectable, directly or indirectly, to a portion of the table. The joint assembly connects with the table adapter about a shaft such that the joint assembly is rotatably adjustable. A head fixation device in the form of a skull clamp is attachable to the joint assembly. The joint assembly generally has a parallelogram shape that has four joints for adjustment where these four joints can be selectively locked or unlocked relative to each other using a single actuator.

14 Claims, 12 Drawing Sheets

(56) References Cited

U.S. PATENT DOCUMENTS

| | | |
|---|---|---|
| 3,835,861 A | 9/1974 | Kees et al. |
| 4,312,336 A | 1/1982 | Danieletto et al. |
| 4,392,645 A | 7/1983 | Westphal |
| 4,457,300 A | 7/1984 | Budde |
| 4,539,979 A | 9/1985 | Bremer |
| 4,541,421 A | 9/1985 | Iversen et al. |
| 4,543,947 A | 10/1985 | Blackstone |
| 4,615,072 A | 10/1986 | Lautenschlager, Jr. |
| 4,667,660 A | 5/1987 | Eingorn |
| 4,796,846 A | 1/1989 | Meier et al. |
| 4,803,976 A | 2/1989 | Frigg et al. |
| 4,807,605 A | 2/1989 | Mattingly |
| 4,827,926 A | 5/1989 | Carol |
| 4,838,264 A | 6/1989 | Bremer et al. |
| 4,971,037 A | 11/1990 | Pelta |
| 5,203,765 A | 4/1993 | Friddle, Jr. |
| 5,276,927 A | 1/1994 | Day |
| 5,284,129 A | 2/1994 | Agbodoe et al. |
| 5,501,685 A | 3/1996 | Spetzler |
| 5,529,358 A | 6/1996 | Dinkler et al. |
| 5,537,704 A | 7/1996 | Dinkler et al. |
| 5,630,805 A | 5/1997 | Ternamian |
| 5,669,912 A | 9/1997 | Spetzler |
| 5,722,978 A | 3/1998 | Jenkins, Jr. |
| 5,865,780 A | 2/1999 | Tuite |
| 5,891,157 A | 4/1999 | Day et al. |
| 5,954,723 A | 9/1999 | Spetzler |
| 6,023,800 A | 2/2000 | Stickley |
| 6,110,182 A | 8/2000 | Mowlai-Ashtiani |
| 6,129,729 A | 10/2000 | Snyder |
| 6,198,961 B1 | 3/2001 | Stern et al. |
| 6,306,146 B1 | 10/2001 | Dinkler |
| D456,510 S | 4/2002 | Spetzler et al. |
| 6,368,332 B1 | 4/2002 | Salcudean et al. |
| 6,557,195 B2 | 5/2003 | Dinkler |
| 6,598,275 B1 | 7/2003 | Kolody et al. |
| 6,659,972 B2 | 12/2003 | Stamper et al. |
| 6,671,904 B2 | 1/2004 | Easterling |
| 6,684,428 B2 | 2/2004 | Grotenhuis et al. |
| 6,805,453 B2 | 10/2004 | Spetzler et al. |
| 6,813,788 B2 | 11/2004 | Dinkler et al. |
| 6,971,617 B2 | 12/2005 | Nguyen |
| 7,045,735 B2 | 5/2006 | Satou et al. |
| 7,232,411 B2 | 6/2007 | Dinkler, II et al. |
| 7,731,141 B2 | 6/2010 | Schuerch |
| 7,836,532 B2 | 11/2010 | Schule |
| 8,051,515 B1 | 11/2011 | Kring |
| 8,256,047 B2 | 9/2012 | Klemm et al. |
| 8,289,406 B2 | 10/2012 | Brackmann |
| 8,302,921 B2 | 11/2012 | Schuerch |
| 2001/0029379 A1 | 10/2001 | Grotehuis |
| 2003/0149429 A1 | 8/2003 | Ferrante et al. |
| 2003/0155748 A1 | 8/2003 | Picard et al. |
| 2009/0249551 A1 | 10/2009 | Klemm et al. |
| 2010/0059064 A1 | 3/2010 | Schuele et al. |
| 2010/0249780 A1 | 9/2010 | Rolfes |

FOREIGN PATENT DOCUMENTS

| | | |
|---|---|---|
| WO | WO 02/85187 | 10/2002 |
| WO | WO 2012/020386 | 2/2012 |

OTHER PUBLICATIONS

European Search Report dated May 11, 2006 for Application No. EP 05292169.

Tuite, Gerald F., M.D. et al., Abstract "Use of an Adjustable Transportable Radiolucent Spinal Immobilization Device in the Comprehensive Management of Cervical Spine Instability, J. of Neurosurgery," vol. 85(6) (Dec. 1996) American Assoc. of Neurosurgeons.

Accessories, Officing Sordina S.p.A.

Codman, "Bookwalter Retractor Kit II", By: Bookwalter, Rochard & Thompson.

Screenshots from www.bicakcilar.com, printed Jan. 28, 2005.

Screenshots from www.integra-ls.com printed Jan. 28, 2005.

Screenshots from www.integra-ls.com printed Dec. 8, 2005.

International Search Report and Written Opinion dated Feb. 19, 2014 for Application No. PCT/IB2013/002389.

English Machine Translation of German Patent DE 91 16 002.

GE Healthcare, Mayfield MR compatible clamp, MR Surgical Suite, available at http://www3.gehealthcare.com/en/products/categories/magnetic_resonance_imaging/mr_surgical_suite#tabs/tab8DDAFB22788244329DF155B67E418F3D, printed Apr. 10, 2015, p. 1-6.

GE Healthcare, Mayfield MR compatible clamp, MR Surgical Suite, available at http://www3.gehealthcare.com/~/media/images/product/product-categories/magnetic-resonance-imaging/mr%20surgical%20suite/mayfield-mr-compatible-clamp.jpg, printed Apr. 10, 2015, p. 1.

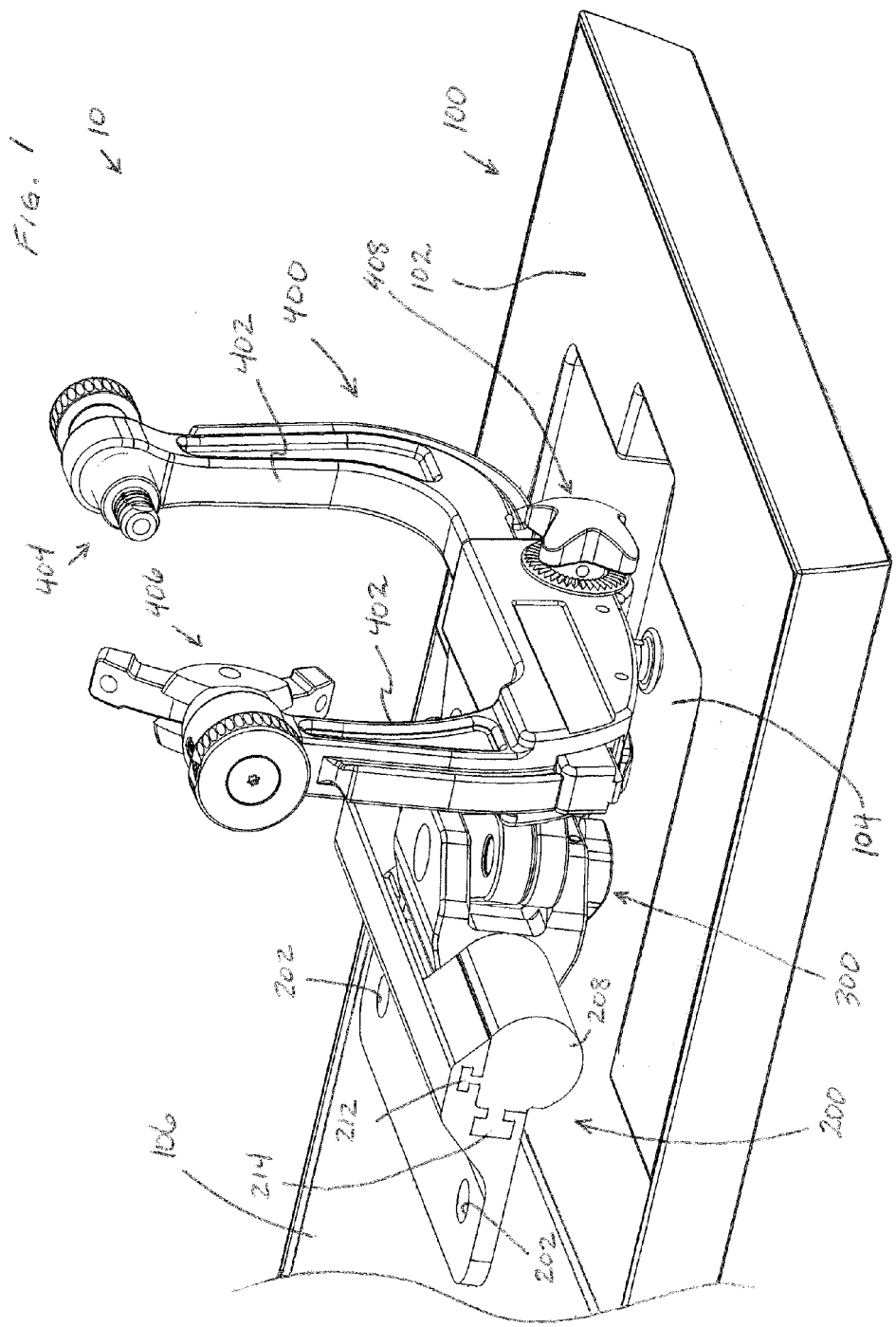

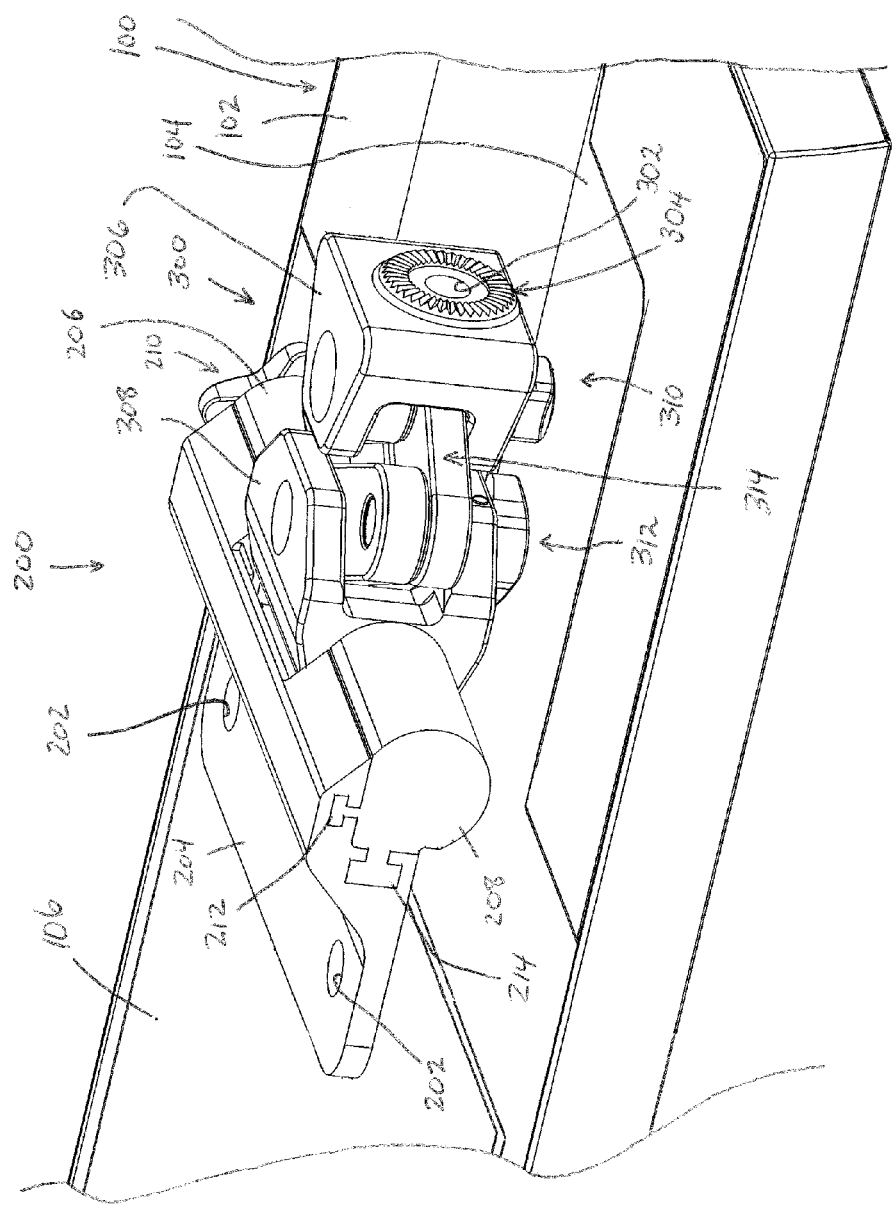

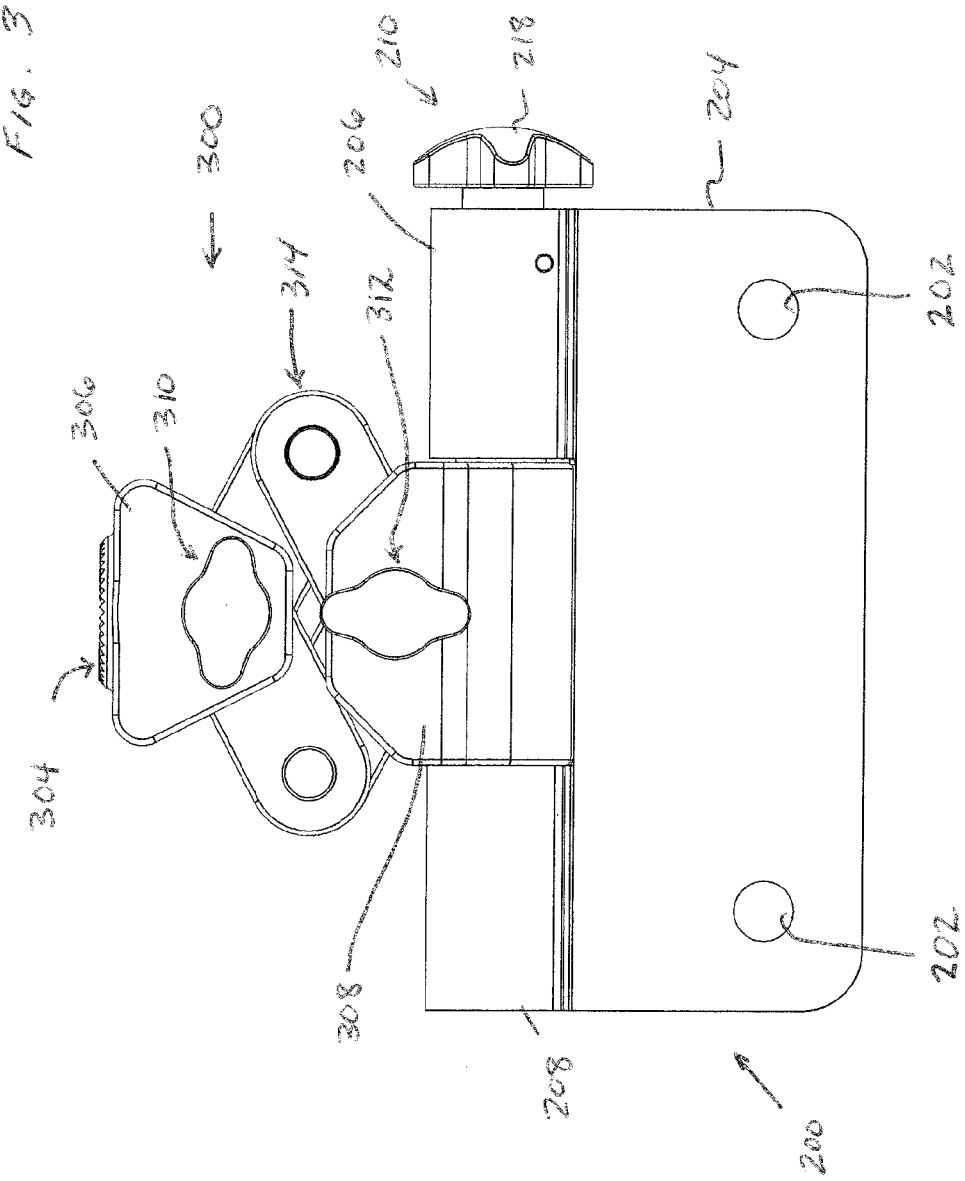

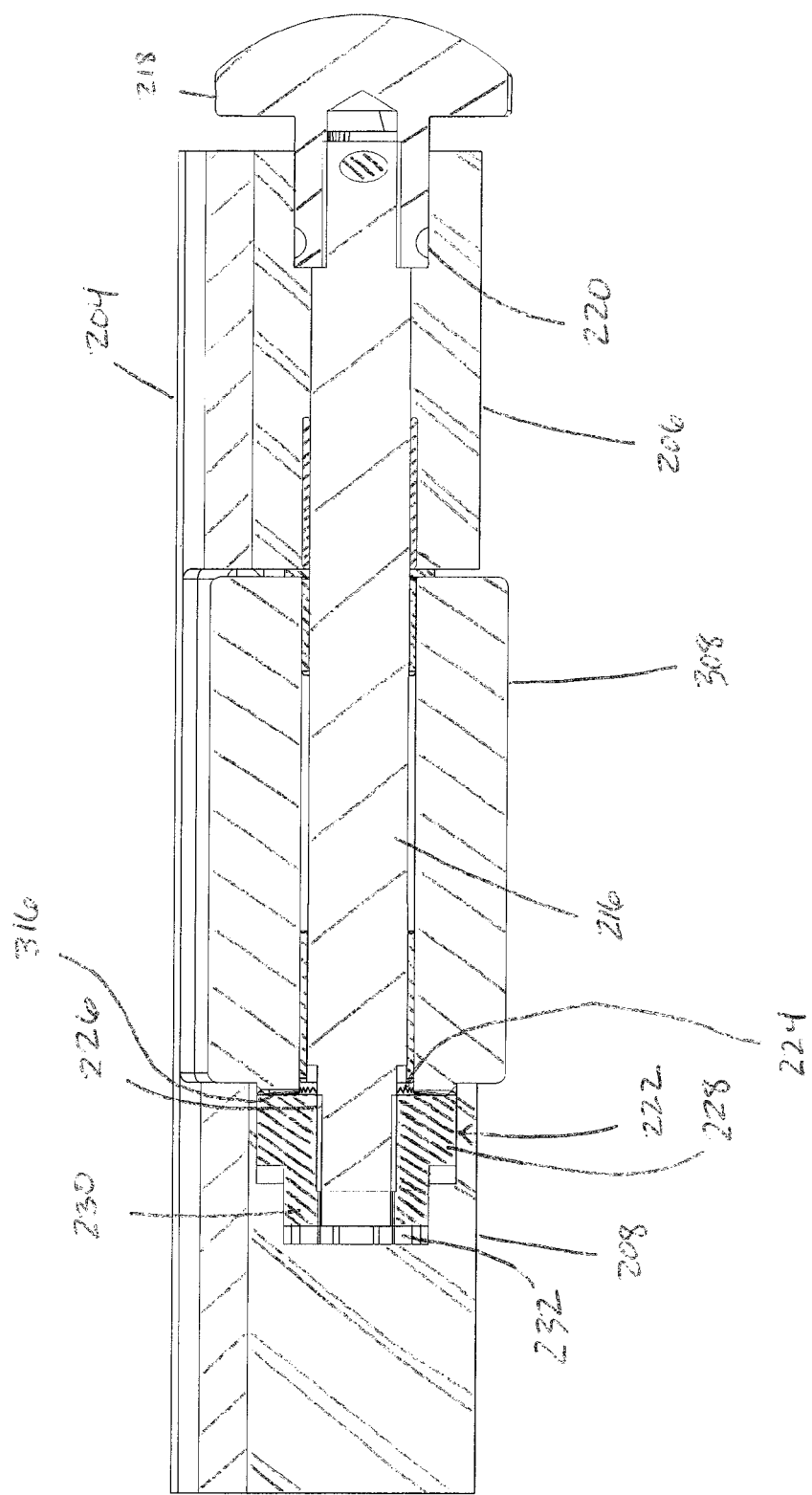

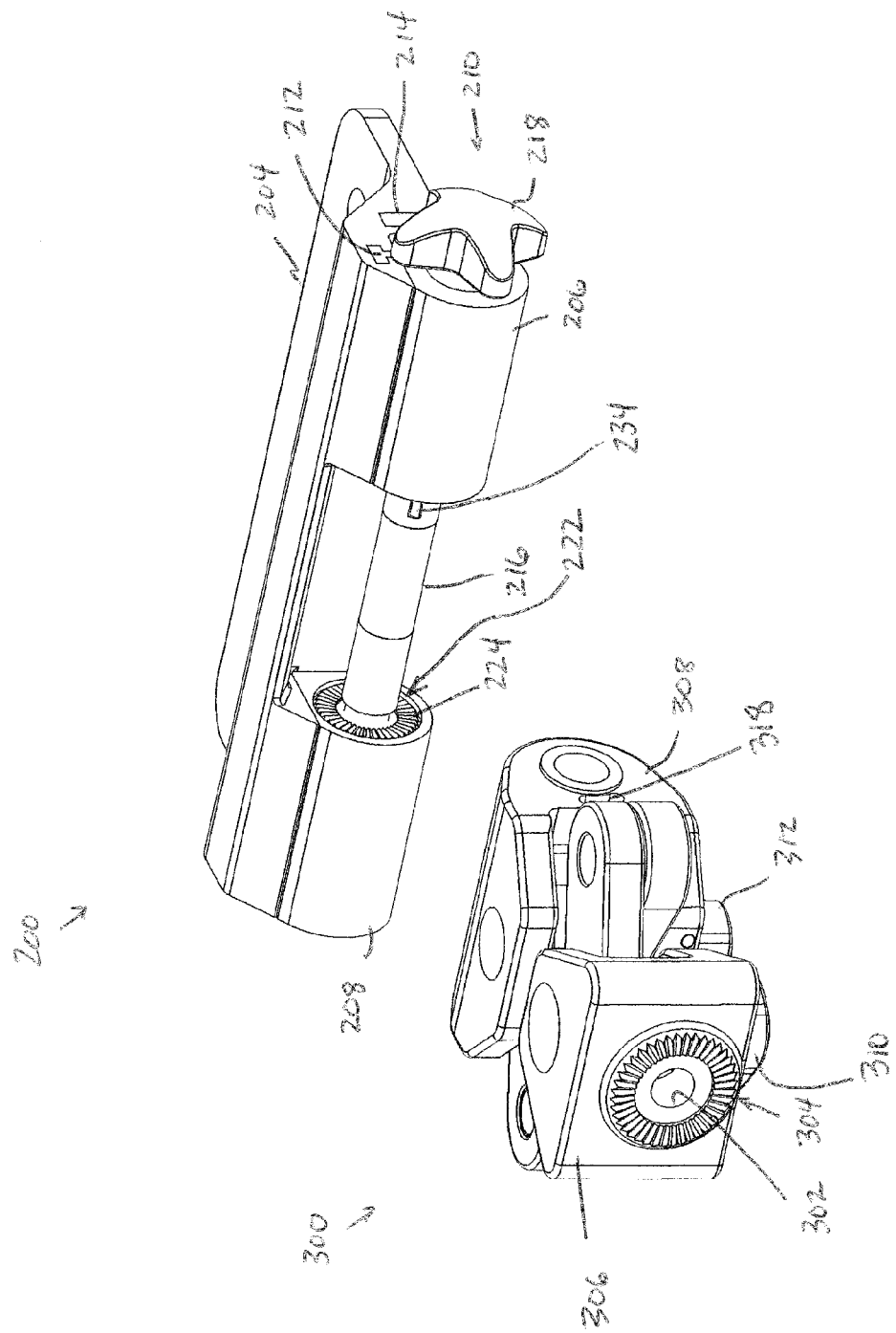

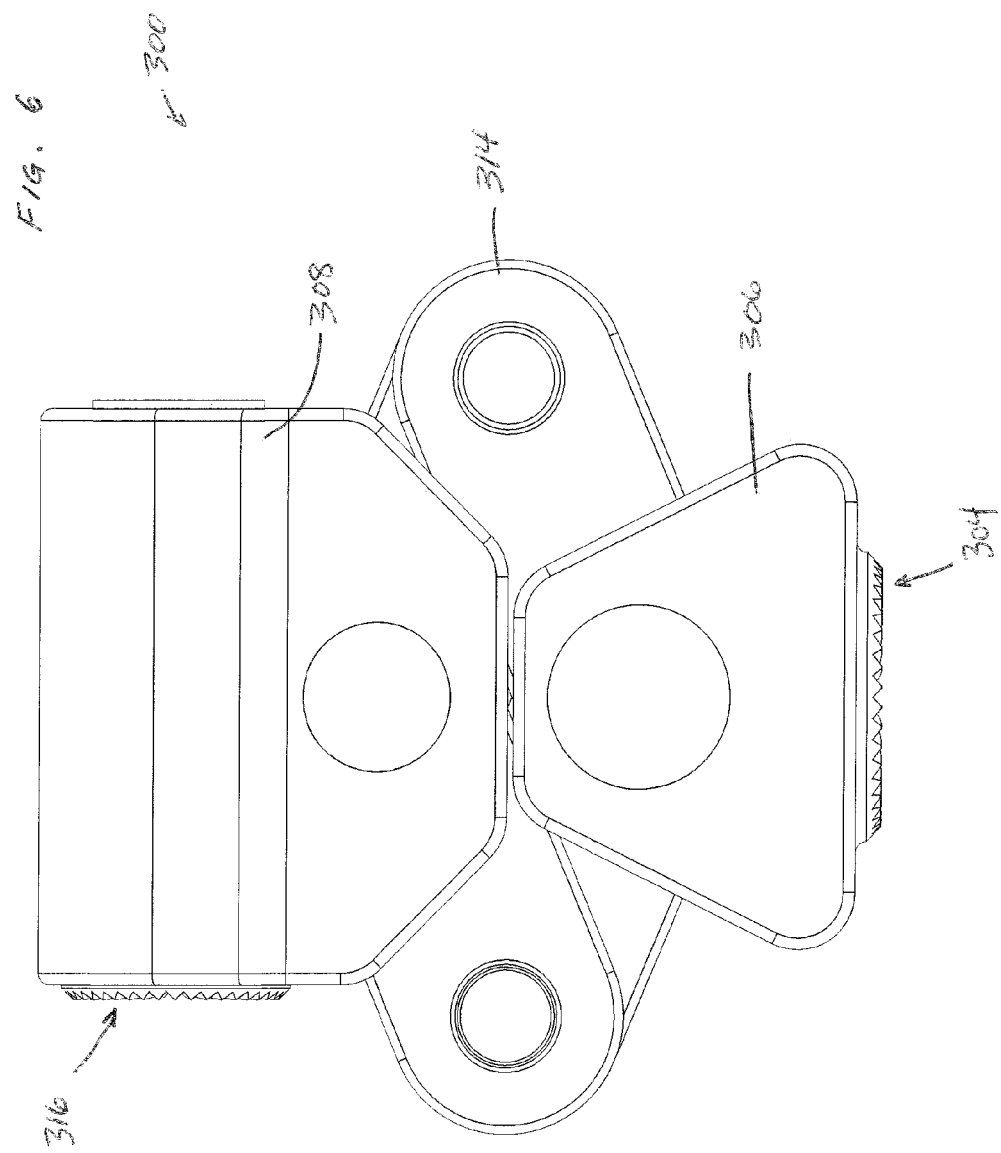

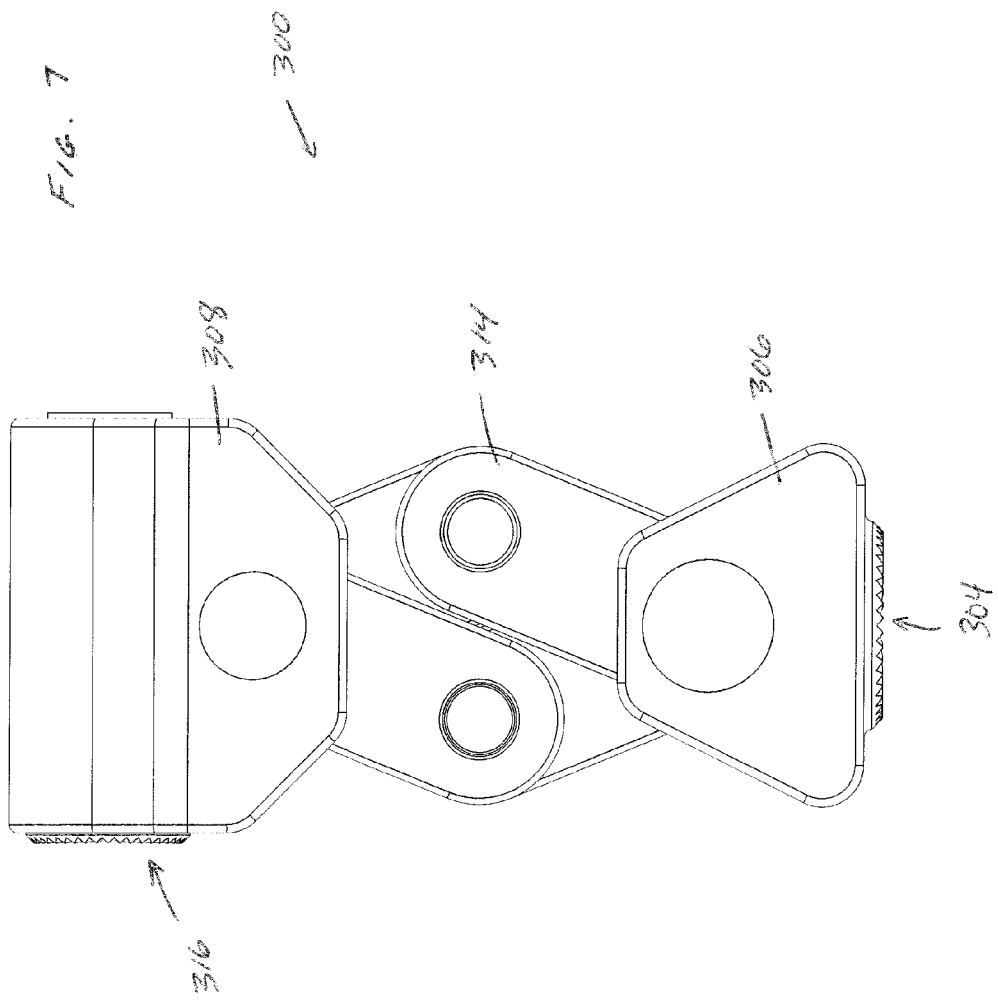

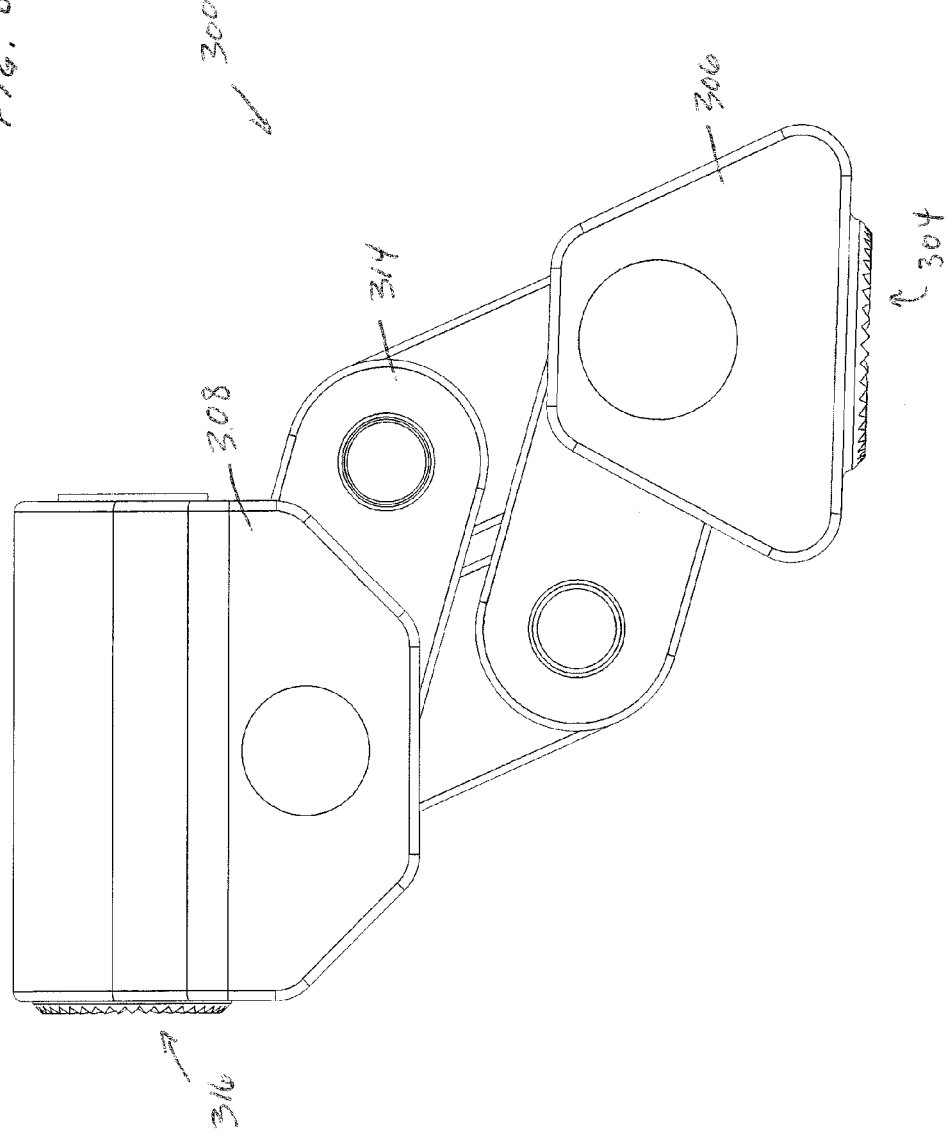

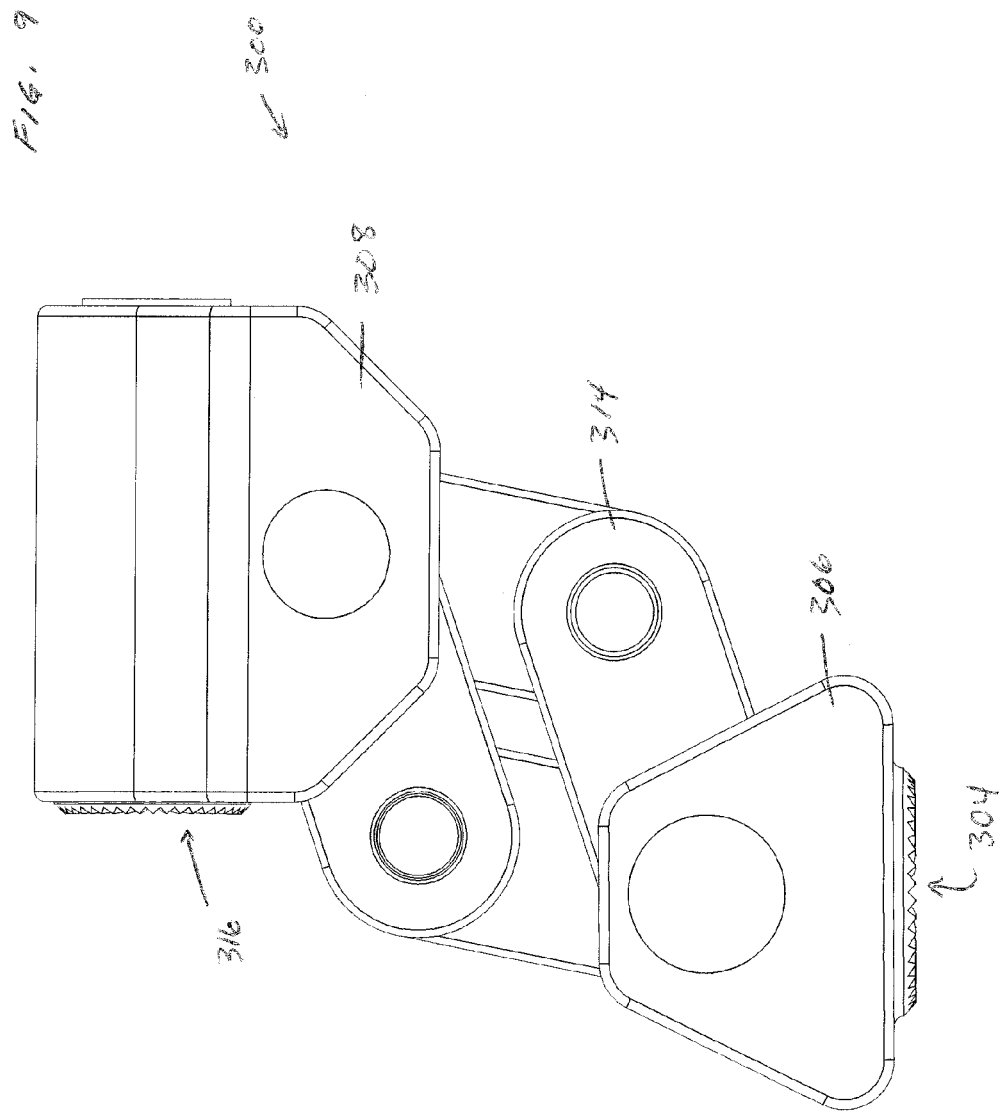

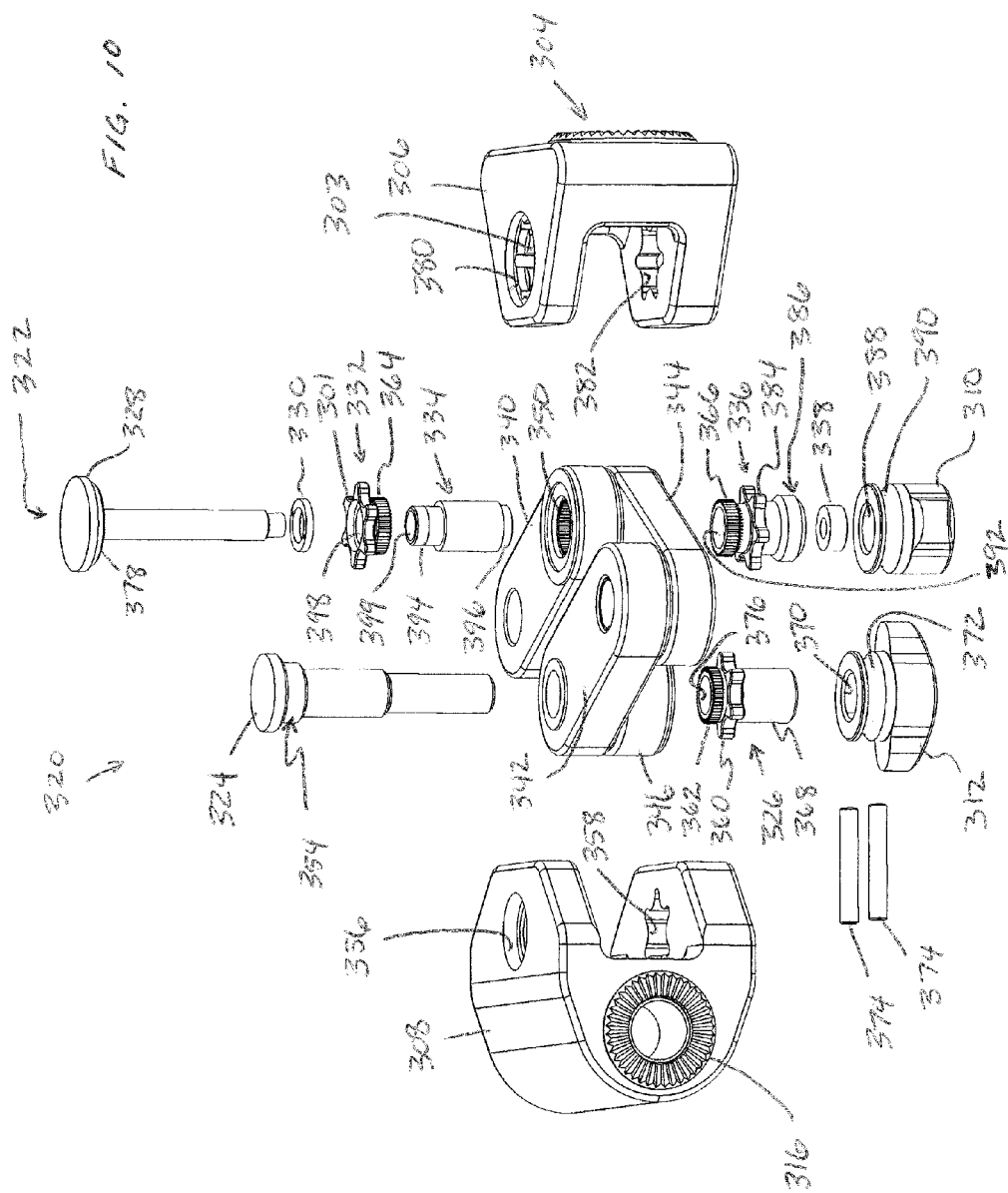

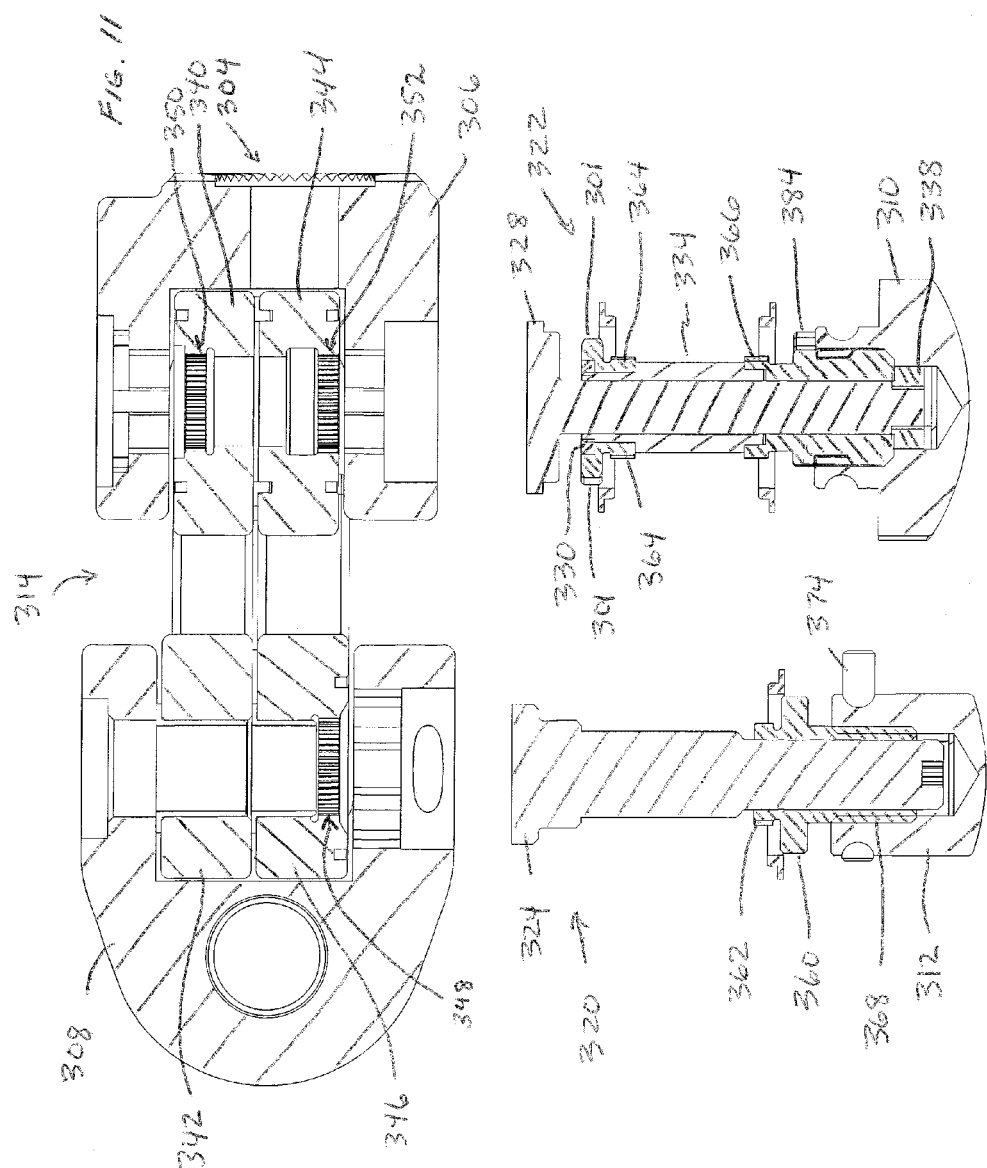

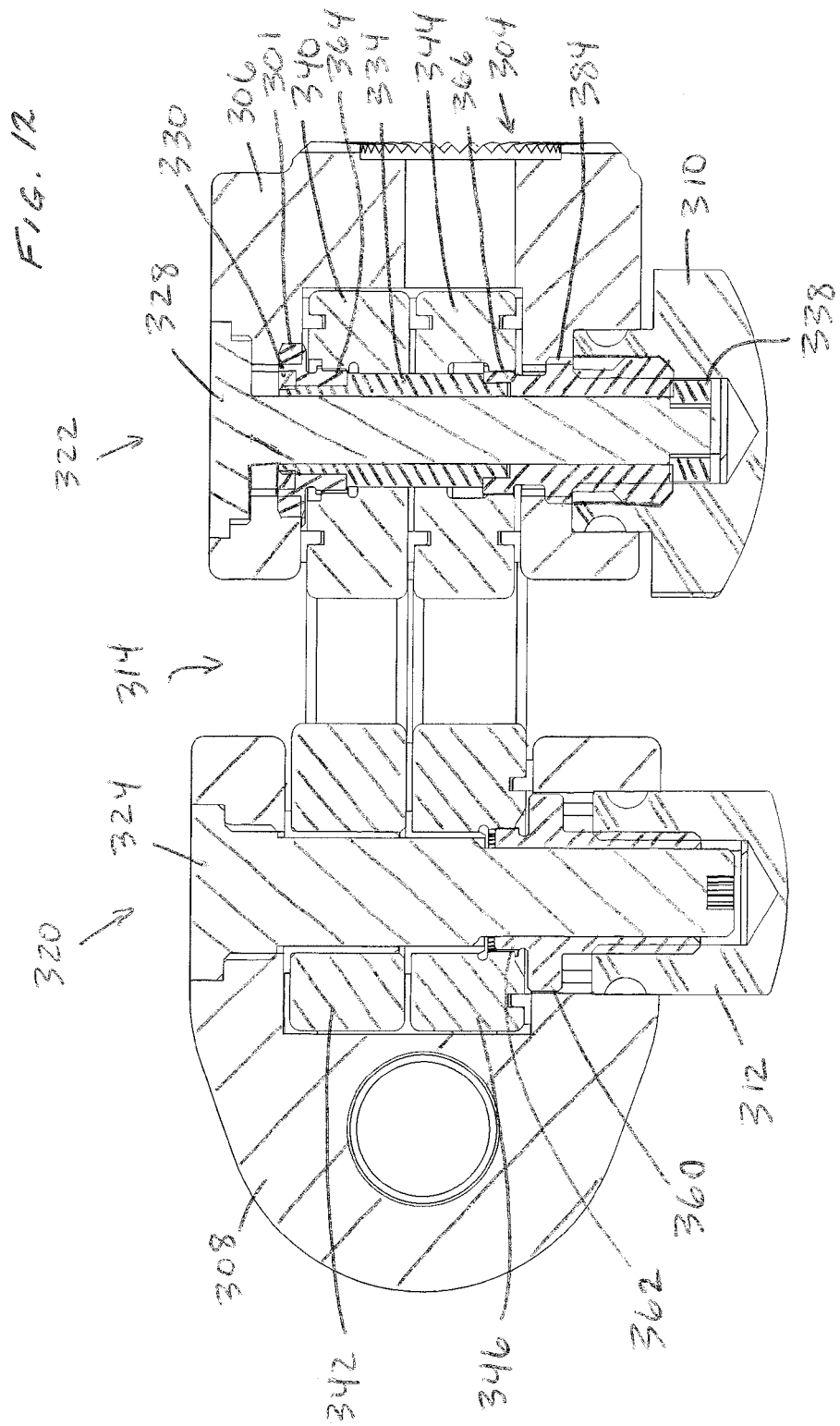

TABLE ADAPTER WITH JOINT ASSEMBLY

PRIORITY

This application claims priority to U.S. Provisional Patent Application Ser. No. 61/694,246, filed Aug. 28, 2012, entitled "TABLE ADAPTER," the disclosure of which is incorporated by reference herein.

BACKGROUND

This disclosure relates to the medical field for head and neck procedures including surgery and imaging, and pertaining particularly to certain medical devices used to stabilize a patient for such procedures. In such procedures a patient can be positioned on a table or board structure (e.g., surgical table, OR table, transport table, transfer board, etc.) and then stabilized using a device such as a headrest, sometimes in the form of a skull clamp. Exemplary skull clamps for use in such systems are available from pro med instruments GmbH in the product line referred to as DORO® Headrest Systems. Where imaging procedures are involved, a stabilized patient can be positioned within the gantry of an MRI machine. In some instances, MRI headcoils can be positioned about the patient's stabilized head to acquire head and/or neck images.

While a variety of headrest systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 1 depicts a perspective view of an exemplary system used for stabilizing a patient.

FIG. 2 depicts a perspective view of the system of FIG. 1, shown without the skull clamp.

FIG. 3 depicts a bottom view of the combined table adapter and joint assembly.

FIG. 4 depicts a front cross section view of the combined table adapter and joint assembly.

FIG. 5 depicts a perspective partially exploded view of the table adapter and joint assembly.

FIG. 6 depicts a top view of the joint assembly, shown in a fully retracted position.

FIG. 7 depicts a top view of the joint assembly, shown in a fully extended position.

FIG. 8 depicts a top view of the joint assembly, shown adjusted to one side.

FIG. 9 depicts a top view of the joint assembly, shown adjusted to the opposite side of that shown in FIG. 8.

FIG. 10 depicts a perspective partially exploded view of the joint assembly.

FIG. 11 depicts a side cross section view of the joint assembly, shown partially exploded.

FIG. 12 depicts a side cross section view of the joint assembly in a closed or locked state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

FIG. 1 illustrates components of an exemplary apparatus (10) that can be used to stabilize a patient's head for a medical procedure. The apparatus (10) comprises a transport table (100), a table adapter (200), a joint assembly (300), and a skull clamp (400).

In the illustrated version, transport table (100) can be used during a medical procedure to transfer a patient from the operating room to an imaging room. Transport table (100) comprises a tabletop (102) and a recessed portion (104). Transport table (100) is configured to be connectable or dockable to a standard OR table. As illustrated in FIGS. 1 and 2, a transfer board (106) is attachable with transport table (100). Transfer board (106) is configured with a generally flat surface upon which a patient can be supported. Furthermore, in the present example, attachable to transfer board (106) is table adapter (200). As described further below, attached with table adapter (200) is joint assembly (300), which is connected with skull clamp (400). With transport table (100) mounted to an OR table, and with transfer board (106) mounted with transport table (100), the patient can moved from the operating room to the imaging room. When ready for imaging, transport table (100), including attached transfer board (106), can be undocked or disconnected from the standard OR table such that the combined transport table (100) and transfer board (106) can be positioned on an MRI machine track or table for sliding into the gantry of the MRI machine. After the imaging is complete the combined transfer board (106) and transport table (100) can again be docked to the OR table and the patient transferred back to the operating room or another location. If further surgical procedure is needed, transfer board (106) can be disconnected from transport table (100) and connected with a standard OR table. With the above described arrangement, the patient can maintain their stabilized position relative to skull clamp (400) during surgery, transport, and imaging procedures.

In the illustrated version, recessed portion (104) of transport table (100) provides space for the attached stabilization components connected with transfer board (106). This can be useful when trying to minimize system height as MRI gantries can present space limitations. However, transport table (100) is not required to have recessed portion (104) in all versions. For example, in some versions, transport table (100) may comprise a solid flat support surface. In some other versions, transport table (100) may comprise a fixed portion that is a solid flat support surface, and another adjustable support portion near the head and neck that can be lowered relative to the fixed portion to compensate for the height of table adapter (200) and joint assembly (300). In view of the teachings herein, other tables and modifications to transport table (100) will be apparent to those of ordinary skill in the art.

In the illustrated version of FIG. 1, skull clamp (400) comprises arms (402) with stabilizing assemblies (404, 406) at each end of arms (402). Stabilizing assemblies (404, 406) are configured to contact a patient's head to stabilize the patient relative to skull clamp (400). Skull clamp (400) further comprises a connector (408) that is configured to attach skull clamp (400) with joint assembly (300). Connector (408) includes a threaded rod (not shown) and starburst interface (not shown) that engage with a threaded bore (302) and starburst interface (304) of joint assembly (300) as seen in FIG. 2. While the illustrated version shows skull clamp (400) as the device that contacts the patient to stabilize them, in other versions skull clamp (400) could be replaced with another head fixation device, e.g., a halo type device. In view of the teachings herein, suitable head fixation devices for use with apparatus (10) will be apparent to those of ordinary skill in the art.

FIG. 2 illustrates combined table adapter (200) and joint assembly (300) connected with transfer board (106) which connects with transport table (100). In the illustrated version, table adapter (200) comprises bores (202). Fasteners (not shown) are used to connect table adapter (200) with transfer board (106). For example, in one version fasteners are bolts or screws that pass through bores (202) and into corresponding bores in transfer board (106). Bores (202) of table adapter (200) and/or the corresponding bores in transfer board (100) may be smooth or threaded depending on the fastener type used to attach table adapter (200) with transfer board (106). In some other versions, table adapter (200) can be connected to structures other than transfer board (106). For instance, table adapter (200) could be connected directly to an OR table, or table adapter (200) could be connected to a base unit or other intermediate structure to an OR or similar table. Still in some versions table adapter (200) can be omitted and joint assembly (300) can connect to a base unit that in turn connects to an OR table, e.g. by the base unit attaching to side rails of the OR table. Still yet, standard table rods can be used with table adapter (200) and/or joint assembly (300). Other ways to connect table adapter (200) and/or joint assembly (300), either directly or indirectly, to a patient support device of some kind will be apparent to those of ordinary skill in the art in view of the teachings herein.

As shown in the illustrated version of FIGS. 2 and 3, joint assembly (300) comprises a distal joint (306) with starburst interface (304) at its distal end, which is configured to connect with skull clamp (400). At its proximal end, joint assembly (300) comprises proximal joint (308), which is configured to connect with table adapter (200). On a bottom side of joint assembly (300) are actuators (310, 312). Actuators (310, 312) extend through distal joint (306) and proximal joint (308) respectively. Actuators (310, 312) further extend through a central joint (314). Central joint (314) is configured as a parallelogram member in the illustrated version. As will be discussed further below, actuators (310, 312) control the adjustability of central joint (314) by selectively locking and unlocking central joint (314) and the attached proximal joint (308) and distal joint (306).

FIGS. 4 and 5 illustrate views of table adapter (200) and joint assembly (300) that show the connection between these components and the adjustment ability also. Table adapter (200) comprises table attachment member (204), first lateral member (206), second lateral member (208), and connector (210). Table attachment member (204) connects with first and second lateral members (206, 208) by use of corresponding engaging features. In the illustrated versions the corresponding engaging features are projections (212, 214) on first and second lateral members (206, 208) and complementary-shaped grooves within table attachment member (204). With this configuration, first and second lateral members (206, 208) can be slid onto table attachment member (204) from each side. In some other versions, first and second lateral members (206, 208) and table attachment member (204) can be a single piece or non-separable pieces one assembled. Other ways to connect first and second lateral members (206, 208) with table attachment member (204) will be apparent to those of ordinary skill in the art in view of the teachings herein.

First lateral member (206) comprises a bore extending through first lateral member (206) and connector (210) comprises shaft (216) that extends through the bore of first later member (206). At one end of shaft (216), actuator (218) is connected. In the illustrated versions, actuator (218) takes the form of a knob. Actuator (218) and shaft (216) are connected such that they are fixed, thereby rotation of actuator (218) produces corresponding rotation of shaft (216). In the present example, actuator (218) is fixed with shaft (216) using a connecting pin. In some versions, shaft (216) can, instead or in addition, be threadably connected with actuator (218).

Actuator (218) comprises groove (220) that is configured to receive a pin (not shown). The pin also fits within a bore within first lateral member (206) such that the pin remains stationary. This configuration secures actuator (218) with first lateral member (206) in a way where actuator (218) can rotate, but does not translate relative to first lateral member (206).

At the end of shaft (216) that is opposite actuator (218), shaft (216) is threaded and threadably connects with locking member (222). Locking member (222) comprises starburst interface (224) that faces the side of proximal joint (308) closest to second lateral member (208). Locking member (222) has threaded bore (226) that extends through locking member (222). Shaft (216) extends within threaded bore (226) and threadably engages with threaded bore (226). Locking member (222) comprises first portion (228) and second portion (230). In the illustrated version, first portion (228) has a cylinder shape. Second portion (230) of locking member (222) has a multi-lobed-shape or star-shape. Second portion (230) may be referred to as a multi-lobed structure or star feature in some instances. Also, in some instances locking member (222), and other locking members described herein may be referred to as a polygon. Threaded bore (226) extends though both first and second portions (228, 230).

As actuator (218) and shaft (216) rotate, locking member (222) does not rotate because second portion (230) of locking member (222) is retained within a recess (232) of second lateral member (208) where recess (232) has a complementary shape to that of second portion (230). In this way, the interference between the second portion (230) and recess (232) prevent rotation of locking member (222). Therefore, when shaft (216) rotates, locking member (222) translates along its threaded connection with shaft (216). From this translation action of locking member (222), starburst interface (224) is moved into or out of engagement with a corresponding starburst interface (316) of joint assembly (300). It is this engagement between starburst interface (224) and starburst interface (316) that secures or locks joint assembly (300) in position relative to table adapter (200). Also, it is this disengagement between starburst interface (224) and starburst interface (316) that permits adjustment or unlocks joint assembly (300) so that joint assembly (300) can be adjustably rotated about shaft (216) to a desired position. In the present example, when assembled, second portion (230) remains in contact with recess (232) both when starburst interface (224) is engaged with a corresponding starburst interface (316) of joint assembly (300), and when starburst interface (224) is not engaged with corresponding starburst interface (316) of joint assembly (300).

Adjusting joint assembly (300) by rotation about shaft (216) provides a height adjustment of skull clamp (400) that attaches to joint assembly (300). Furthermore, this adjustment also provides the ability to adjust the angle of skull clamp (400). For instance, skull clamp (400), in some versions, can be generally perpendicular to transfer board (106), while in other versions skull clamp (400) can have another suitable angle with transfer board (106) through the rotatable adjustment described here.

Referring to FIG. 5, table adapter (200) also comprises pin (234) that is configured to be received within slot (318) on proximal joint (308) of joint assembly (300). This insertion of pin (234) within slot (318) defines a range of rotatable adjustability of joint assembly (300) about shaft (216) of table adapter (200). In some versions, pin (234) and slot (318) may be omitted altogether. Also, in versions including pin (234) and slot (318), these components act as a lower stop such that joint assembly (300) and skull clamp (400) can be rested on pin (234) such that joint assembly (300) does not inadvertently rotate to a bottom position when, e.g., actuator (218) is used to unlock locking member (222) relative to joint assembly (300).

FIGS. 6-9 illustrate joint assembly (300), showing a range of adjustment. As shown in the illustrated version of FIG. 6, joint assembly (300) can be adjusted to a fully retracted position. In this position, central joint (314) has a collapsed configuration such that the distance between proximal joint (308) and distal joint (306) is at a minimum. As shown in the illustrated version of FIG. 7, joint assembly (300) can be adjusted to a fully extended position. In this position, centrally joint (314) has an extended configuration such that the distance between proximal joint (308) and distal joint (306) is at a maximum. As shown in the illustrated versions of FIGS. 8 and 9, joint assembly (300) can be adjusted to a left or right position (also sometimes referred to as side to side or lateral adjustment). This side to side or lateral adjustment occurs by central joint (314) rotating about the axis defined by bolt (324) and/or bolt (328) as described further below. Between the extended and collapsed positions, and the side to side positions, joint assembly (300) can be considered as being adjustable in at least two directions. From the range of adjustment of joint assembly (300), it is possible make the above range of adjustments, or anywhere in between. It is further possible, when making such adjustments, to maintain starburst interface (304) and starburst interface (316) in a generally perpendicular orientation. In other instances, distal joint (306) can be adjusted rotatably such that starburst interface (304) has some other desired orientation relative to the orientation of starburst interface (316). For example, distal joint (306) can be adjusted such that starburst interface (304) is at about a 45 degree angle with starburst interface (316). Other angles and arrangement of starburst interfaces (304, 316) will be apparent to those of ordinary skill in the art in view of the teachings herein.

FIGS. 10-12 illustrate more detailed views of joint assembly (300) and show its locking and adjustment features and structures. Referring to FIG. 10, central joint (314) of joint assembly (300) comprises proximal connector (320) and distal connector (322). Proximal connector (320) comprises bolt (324), locking member (326), and actuator (312). Distal connector (322) comprises bolt (328), upper nut (330), upper locking member (332), spacer (334), lower locking member (336), lower nut (338), and actuator (310). Proximal connector (320) and distal connector (322) are actuated to alter the state of joint assembly (300) from locked or non-adjustable to unlocked or adjustable. Furthermore, when joint assembly (300) is in the locked state, as will be further described below, joint assembly (300) may still be adjusted rotationally relative to table adapter (200) as discussed above.

Central joint (314) of joint assembly (300) further comprises arms (340, 342, 344, 346) that can adjust relative to one another. Each arm (340, 342, 344, 346) comprises two bores, one at each end. Each arm (340, 342, 344, 346) connects with two other arms (340, 342, 244, 346) via alignment of the bores and a suitable fastener. At the proximal-most (direction closest to table adapter (200)) region of arms (342, 346), arms (342, 246) connect with proximal joint (308). At the distal-most (direction closest to skull clamp (400)) region of arms (340, 344), arms (340, 344) connect with distal joint (306). At the middle region of central joint (314), arms (340, 346) and arms (342, 344) rotatably connect to one another via bearings or other suitable fastener that permits an adjustable rotatable connection.

Referring to FIG. 11, the proximal bore of arm (346) comprises a locking surface (348). Locking surface (348) comprises teeth that are configured to engage complementary teeth on gear portion (362) of locking member (326). Similarly, distal bores of arms (340, 344) comprise locking surfaces (350, 352). Locking surface (350) comprises teeth that are configured to engage complementary teeth on gear portion (364) of upper locking member (332). Locking surface (352) comprises teeth that are configured to engage complementary teeth on gear portion (366) of lower locking member (336). As shown in the illustrated version, other regions of bores of arms (340, 342, 344, 346) can have smooth surfaces.

Referring again to FIG. 10, bolt (324) of proximal connector (320) comprises threaded portion (354) that threadably engages threads within bore (356) of proximal joint (308). Proximal joint (308) further includes bore (358) that is shaped to complement multi-lobe portion or star feature (360) of locking member (326). When assembled, multi-lobe portion (360) is received within bore (358), and the contact between multi-lobe portion (360) and bore (358) prevents rotation of locking member (326). Locking member (326) comprises threaded portion (368) that engages threaded bore (370) of actuator (312). Actuator (312) comprises groove (372) that receives pins (374) that are secured within a lower portion of proximal joint (308). When assembled, actuator (312) rotates in place without translating. Furthermore, locking member (326) can translate along the axis defined by bolt (324) based on its threaded engagement with bore (370) and rotation of actuator (312). Locking member (326) comprises bore (376) through which bolt (324) extends when assembled. In operation, the rotation of actuator (312) causes locking member (326) to translate up or down along bolt (324) depending on the direction actuator (312) is rotated. When gear portion (362) of locking member (326) is aligned and engaged with locking surface (348) of arm (346), the joint between arm (346) and arm (342) is locked. When gear portion (362) of locking member (326) is not aligned and not engaged with locking surface (348) of arm (346), the joint between arm (346) and arm (342) is unlocked. In this unlocked state, gear portion (362) of locking member (326) is positioned below locking surface (348) due to downward translation of locking member (326).

Referring again to FIGS. 10-12, bolt (328) of distal connector (322) comprises threaded portion (378) that threadably engages threads within bore (380) of distal joint (306). In some versions, the end of bolt (328) is also threaded and engages a threaded nut (338) that seats within bore (388) of actuator (310). This engagement or engagements retain bolt (328) in place. Distal joint (306) further includes bore (382) that is shaped to complement multi-lobe portion or star feature (384) of lower locking member (336). When assembled, multi-lobe portion (384) is received within bore (382), and the contact between multi-lobe portion (384) and bore (382) prevents rotation of locking member (336). Locking member (336) comprises threaded portion (386) that engages threaded bore (388) of actuator (310). Actuator (310) comprises groove (390) that, in some versions, receives one or more pins (not shown) similar to pins (374) that are secured within a lower portion of distal joint (306). When assembled, actuator (310) rotates in place without translating. Furthermore, lower locking member (336) can translate along the axis defined by bolt (328) based on its threaded engagement with bore (388) and rotation of actuator (310). Lower locking member (336) comprises bore (392) through which bolt (328) extends when assembled. In operation, the rotation of actuator (310) causes lower locking member (336) to translate up or down along bolt (328) depending on the direction actuator (310) is rotated. When gear portion (366) of lower locking member (336) is aligned and engaged with locking surface (352) of arm (344), the joint between arm (344) and arm (340) is locked. When gear portion (366) of lower locking member (336) is not aligned and not engaged with locking surface (352) of arm (344), the joint between arm (344) and arm (340) is unlocked. In this unlocked state, gear portion (366) of lower locking member (336) is positioned above locking surface (352) due to upward translation of lower locking member (336).

In the illustrated version, distal connector (322) further comprises a spacer or tube (334) adjacent to lower locking member (336). Spacer (334) comprises threaded upper portion (394) and threaded lower portion (396). Lower portion (396) is secured with an upper portion of bore (392) by a threaded connection or other suitable connection that joins spacer (334) with lower locking member (336). Threaded upper portion (394) extends through bore (398) of upper locking member (332) and threadably connects with upper nut (330). Upper nut (330) seats within a recess within an upper part of bore (398) of upper locking member (332). The threaded connection between spacer (334) and upper nut (330) effectively connects upper locking member (332) with spacer (334). Spacer (334) further comprises bore (399) such that when assembled, bolt (328) extends through upper nut (330), upper locking member (332), spacer (334), and lower locking member (336). With this configuration, lower locking member (336) and upper locking member (332) are effectively indirectly connected such that translation of lower locking member (336) will result in the same translation (magnitude and direction) of upper locking member (332). While the illustrated version includes spacer (334) and upper locking member (332), these are not required in all versions. For example, in some other versions, distal connector (322) can have only one locking member, similar to proximal connector (320).

Upper locking member (332) further comprises multi-lobe portion or star feature (301). Bore (380) includes lower portion (303) having a complementary shape to multi-lobe portion (301). When assembled, multi-lobe portion (301) is received within lower portion (303) of bore (380). Again, the contact between the complementary shapes of multi-lobe portion (301) and lower portion (303) prevents upper locking member (332) from rotating, while at the same time permitting upper locking member (332) to translate.

In operation, as actuator (310) is rotated, lower locking member (336) translates along the axis defined by bolt (328) based on its threaded connection with bore (388) of actuator (310). Spacer (334) and upper locking member (332) translate also as these components are indirectly connected with lower locking member (336) as described above. Therefore, the connection between spacer (334) and upper locking member (332) and spacer (334) and lower locking member (336) causes upper locking member (332) to translate in unison with lower locking member (336). In the present example, this translation in unison applies to both upward translation and downward translation, and the direction of translation is dictated by the direction of rotation of actuator (310).

The translating movement of lower and upper locking members (336, 332) causes teeth of gear portion (364) of upper locking member (332) to engage or disengage (as the case may be depending on the direction of knob rotation and direction of translation of the related components) locking surface (350) on the distal side of arm (340). Similarly, translating movement of lower and upper locking members (336, 332) causes teeth of gear portion (366) of lower locking member (336) to engage or disengage (as the case may be depending on the direction of knob rotation and direction of translation of the related components) locking surface (352) on the distal side of arm (344). In the illustrated version, when distal connector (322) is in an unlocked state, lower locking member (336) and upper locking member (332) are positioned such that gear portions (364, 366) are positioned above respective locking surfaces (350, 352). When distal connector (322) is in a locked state, lower locking member (336) and upper locking member (332) are translated such that they are positioned such that gear portions (364, 366) are positioned in alignment with respective locking surfaces (350, 352). In some other versions, the threaded regions of the components comprising distal connector (322) can be modified to control translation of lower locking member (336) and upper locking member (332) such that they translate in opposite directions when actuator (310) is actuated. In such an example, spacer (334) would not act to connect lower and upper locking members (336, 332). Still other ways to control translation of lower and upper locking members (336, 332) will be apparent to those of ordinary skill in the art in view of the teachings herein.

The locking and unlocking action of the distal and proximal connectors (322, 320) of joint assembly (300) described above make joint assembly (300) adjustable as shown in FIGS. 6-9. By way of further example, having only one of proximal connector (320) and distal connector (322) in the locked state, while the other is in the unlocked state will allow for rotatable adjustment about the axis defined by the bolt of the unlocked one of the connectors. For instance, if proximal connector (320) is unlocked and distal connector (322) is locked, then central joint (314) can be rotatably adjusted about the bolt (324). In other words central joint (314) can be adjusted laterally, or from side to side as shown in FIGS. 8 and 9. If instead proximal connector (320) is locked and distal connector (322) is unlocked, then distal joint (306) can be rotatably adjusted about bolt (328). In other words, the angle of starburst (316) can be rotatably adjusted to adjust an attached skull clamp for example. To adjust central joint (314) from a collapsed state to an extended state as shown in FIGS. 6 and 7 both proximal connector (320) and distal connector (322) must be in the unlocked state. That is, to change the shape of central joint (314) both connectors (320, 322) must be unlocked.

With the above configuration, central joint (314) comprises four distinct joints where the bores of each arm (340, 342, 344, 346) align. Furthermore, as described, joint assembly (300) is configured such that, in the illustrated version, only one of two locking and unlocking actuators (310, 312) are needed to lock and unlock all four distinct joints. In other words, locking just one of connectors (320, 322) using the associated actuator (310, 312) will secure or lock the position of the four joints of central joint (314) relative to one another.

All or some of the components of table adapter (200), joint assembly (300), and skull clamp (400) can be made from materials that include, aluminum, titanium, stainless steel, ceramic, plastic, or radiolucent materials. Other materials for construction of the components described herein will be apparent to those of ordinary skill in the art in view of the teachings herein.

In some versions, distal joint (306) may be modified with an additional range of adjustability. In particular, where starburst (304) connects with skull clamp (400), another joint may intervene between starburst (304) and skull clamp (400) such that if joint assembly (300) is rotated relative to table adapter (200), then skull clamp (400) can be adjusted to maintain a perpendicular position of skull clamp (400) to table (100). This and other modifications will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, while certain terms have been used in this description to describe certain structures, such terms should be construed broadly. For instance, the bores described herein, can in many circumstances be synonymous with terms like openings, passages, holes, among others.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for use in a medical procedure involving stabilizing a patient's head relative to a table, the apparatus comprising:
    (a) an adapter configured to connect with the table;
    (b) a joint assembly configured to connect with a distal end of the adapter, wherein the joint assembly is selectively rotatably adjustable relative to the adapter;
    (c) a head fixation device configured to connect with the joint assembly; wherein the joint assembly is further adjustable in at least two directions for positioning the head fixation device, wherein the joint assembly is configured to provide for longitudinal translation of the head fixation device toward and away from the distal end of the adapter; and
    (d) wherein the adapter comprises:
        (i) a shaft, wherein the joint assembly is positioned on, and selectively rotatable about, the shaft, and
        (ii) a first starburst interface, wherein the first starburst interface is configured to selectively engage a second starburst interface of the joint assembly.

2. The apparatus of claim 1, wherein the first starburst interface of the adapter translates in response to rotation of the shaft.

3. An apparatus for use in a medical procedure involving stabilizing a patient's head relative to a table, the apparatus comprising:
    (a) an adapter configured to connect with the table;
    (b) a joint assembly configured to connect with a distal end of the adapter, wherein the joint assembly is selectively rotatable adjustable relative to the adapter;
    (c) a head fixation device configured to connect with the joint assembly; wherein the joint assembly is further adjustable in at least two directions for positioning the head fixation device, wherein the joint assembly is configured to provide for longitudinal translation of the head fixation device toward and away from the distal end of the adapter; and
    (d) wherein the joint assembly comprises:
        (i) a distal joint, wherein the distal joint connects with the head fixation device,
        (ii) a proximal joint, wherein the proximal joint connects with the adapter, and
        (iii) a central joint, wherein the central joint connects with the distal joint and the proximal joint.

4. The apparatus of claim 3, wherein the adapter comprises a pin, wherein the joint assembly comprises a slot, wherein the slot is configured to receive the pin, and wherein the pin and the slot define a range of rotatable adjustability of the joint assembly relative to the adapter.

5. The apparatus of claim 3, wherein the central joint comprises a parallelogram shape.

6. The apparatus of claim 3, wherein the central joint comprises:
    (a) a plurality of arms, wherein the plurality of arms are configurable in a parallelogram shape;
    (b) a first connector, wherein the first connector is configured to permit selective adjustment of the plurality of arms; and
    (c) a second connector, wherein the second connector is configured to permit selective adjustment of the plurality of arms.

7. The apparatus of claim 3, wherein the joint assembly comprises:
    (a) a plurality of arms having a plurality of bores;
    (b) a first connector comprising a first locking member, wherein the first locking member comprises a first gear portion configured to selectively engage a first locking surface of a first select one of the plurality of bores; and
    (c) a second connector comprising a second locking member, wherein the second locking member comprises a second gear portion configured to selectively engage a second locking surface of a second select one of the plurality of bores.

8. The apparatus of claim 7, wherein the second connector further comprises a third locking member, wherein the third locking member comprises a third gear portion configured to selectively engage a third locking surface of a third select one of the plurality of bores.

9. The apparatus of claim 7, wherein the first and second locking members translate within the plurality of bores to selectively lock and unlock the joint assembly.

10. An apparatus for use in a medical procedure involving stabilizing a patient's head relative to a table, the apparatus comprising:
   (a) an adapter configured to connect with the table;
   (b) a joint assembly configured to connect with a distal end of the adapter, wherein the joint assembly is selectively rotatably adjustable relative to the adapter;
   (c) a head fixation device configured to connect with the joint assembly; wherein the joint assembly is further adjustable in at least two directions for positioning the head fixation device, wherein the joint assembly is configured to provide for longitudinal translation of the head fixation device toward and away from the distal end of the adapter; and
   (d) wherein the joint assembly comprises a central joint, wherein the central joint comprises four joints for adjusting the joint assembly.

11. The apparatus of claim 10, wherein the four joints for adjustment are lockable using a single actuator.

12. An apparatus for use with a head fixation device in a medical procedure involving stabilizing and positioning a patient's head relative to a table, the apparatus comprising:
   (a) an adapter connectable to the table; and
   (b) a joint assembly connectable at a first end to the adapter and connectable at a second end to the head fixation device, wherein the joint assembly is rotatably, laterally, and longitudinally adjustable relative to the adapter; and
   (c) a pair of actuators connected with the joint assembly, wherein the actuators are configured to selectively lock and unlock the joint assembly permitting adjustment of the joint assembly both laterally and longitudinally relative to the adapter.

13. The apparatus of claim 12, wherein the adapter and the joint assembly are comprised of radiolucent materials.

14. The apparatus of claim 12, wherein the head fixation device comprises a skull clamp.

* * * * *

UNITED STATES PATENT AND TRADEMARK OFFICE
CERTIFICATE OF CORRECTION

| | | |
|---|---|---|
| PATENT NO. | : 9,216,126 B2 | Page 1 of 1 |
| APPLICATION NO. | : 14/012868 | |
| DATED | : December 22, 2015 | |
| INVENTOR(S) | : Matthias E. Schuele et al. | |

It is certified that error appears in the above-identified patent and that said Letters Patent is hereby corrected as shown below:

IN THE CLAIMS

Column 10, claim 3, line 19, replace the text "selectively rotatable adjustable" with --selectively rotatably adjustable--.

Signed and Sealed this
Twelfth Day of April, 2016

Michelle K. Lee
*Director of the United States Patent and Trademark Office*